US00PP36872P3

(12) United States Plant Patent
Byrne et al.

(10) Patent No.: US PP36,872 P3
(45) Date of Patent: Aug. 5, 2025

(54) PEACH TREE NAMED 'Flat Delight Three'

(50) Latin Name: *Prunus persica*
Varietal Denomination: Flat Delight Three

(71) Applicant: The Texas A&M University System, College Station, TX (US)

(72) Inventors: David Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 18/445,578

(22) Filed: Oct. 25, 2023

(65) Prior Publication Data

US 2025/0143196 P1 May 1, 2025

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
See application file for complete search history.

(56) References Cited

U.S. PATENT DOCUMENTS

PP28,077 P3 6/2017 Byrne et al.

OTHER PUBLICATIONS

Rawandoozi, 2019, QTL Mapping Through Pedigree-Based Analysis for Six Phenological and Quality Traits in Peach (Retrieved online Nov. 16, 2024 at https://oaktrust.library.tamu.edu/items/5f093264-fa8c-40af-b718-8df61fc95576) (Year: 2019).*

Byrne et al., "'Smooth Delight One' and 'Smooth Delight Two', Medium-chill Subacid Nectarines," HortScience, Dec. 2014, vol. 49, No. 12, pp. 1593-1594.

* cited by examiner

*Primary Examiner* — Shubo (Joe) Zhou
*Assistant Examiner* — Zachariah Allan Kay
(74) *Attorney, Agent, or Firm* — McKee, Voorhees & Sease, PLC

(57) ABSTRACT

Disclosed is a new variety of *Prunus persica* named 'Flat Delight Three'. This new variety, which requires approximately 350 chilling units of dormancy, is considered to be a peach tree of early season maturity, which produces subacid, white-fleshed flat (pantao) fruit that are firm, with the skin covered on 50-80% of its surface with a dark pink to dark maroon blush over a light yellow ground color, and suitable for both local and long-distance shipping.

4 Drawing Sheets

FIELD OF THE INVENTION

This invention relates to peach trees and, more specifically, to peach trees referred to as a variety of *Prunus persica* named 'Flat Delight Three', which requires approximately 350 chilling units of dormancy, produces a firm clingstone white-fleshed subacid flat peach that matures early in the season.

SUMMARY OF THE INVENTION

The 'Flat Delight Three' peach is characterized by producing subacid white-fleshed flat peach fruit that ripens in the early May; is firm and has a 50% to 80% dark pink to dark maroon blush over a light yellow ground color. In this regard, the present variety of peach tree bears fruit that are ripe for commercial harvesting and shipment in early May, when the fruit is grown in the medium chill zone of Texas. 'Flat Delight Three' ripens 4 to 8 days earlier than its parent, 'Smooth Delight One' a medium chill subacid white-fleshed nectarine (Byrne and Anderson, 2014; U.S. Plant Pat. No. 28,077, 6 Jun. 2017) and 28-37 days before its parent 'Galaxy' a non-patented, subacid, white-fleshed flat peach (Ramming, 2005). Additionally, the new variety exhibits the potential to be commercialized in regions that have chilling requirements that are relatively low.

ORIGIN OF THE VARIETY

The present peach tree was the result of an ongoing Stone Fruit Breeding Program at College Station, Brazos County, Texas. To this end, controlled crosses are made each year to produce seedling populations from which improved progenies are evaluated and selected.

'Flat Delight Three' (breeding selection number TX3B376LWP) was originated at College Station, Texas in 2007, and was chosen from a population of seedlings that resulted from embryo-rescued seed from a hand pollination between 'Smooth Delight One' (TX2A232LWN) a subacid, white-fleshed nectarine as the female parent and 'Galaxy' a subacid white-fleshed flat peach as the pollen parent.

The female parent, 'Smooth Delight One' differs from the selection as it ripens 4-8 (mean=6.2) days after 'Flat Delight Three', and is a round nectarine rather than a flat or pantao peach. The pollen parent, 'Galaxy' differs from the selection in that it has non-showy blooms that open 4-8 (mean 6.7) days later, globose leaf glands and larger fruit that ripen 28-37 (mean of 33) days after 'Flat Delight Three'.

Resulting seed from this cross were planted in 2008 at an experimental field in College Station, TX. 'Flat Delight Three' was marked for subsequent observation and noted as having exceptional characteristics in 2010. Two-year and older trees of the variety were subsequently evaluated during the 2014 through 2020 fruit growing seasons in Texas (Fairfield and College Station).

ASEXUAL REPRODUCTION OF THE VARIETY

'Flat Delight Three' was bud grafted onto virus-free Nemaguard ("The Brooks and Olmo Register of Fruit and Nut Varieties," 3rd Ed., American Society of Horticultural Science Press, Alexandria, VA, 1997) peach rootstock in June 2010 at the nursery site in Oakdale, CA. The variety was subsequently planted at the experimental orchard in two sites in Texas (College Station and Fairfield). Fruit from the resulting propagation has been evaluated during the period from 2014 to 2020 fruit seasons. This evaluation clearly demonstrated that the re-propagated trees were true to the characteristics of the original seedling in all observable aspects.

PHOTOGRAPHS OF THE VARIETY

This new variety of peach tree is illustrated by the accompanying photographic drawings and depicts the plant by the best possible color representation using color photography, wherein:

FIG. 1 is a color photograph of a characteristic twig bearing typical leaves from a tree in College Station orchard, Harvested Jul. 19, 2023; several leaves showing both the dorsal and ventral coloration.

FIG. 2. Fruit of the 'Flat Delight Three' harvested May 3, 2023 in orchard in Fairfield TX, showing axial and suture plane to illustrate the flesh and stone characteristics thereof.

BOTANICAL DESCRIPTION OF THE VARIETY

Figure 1:
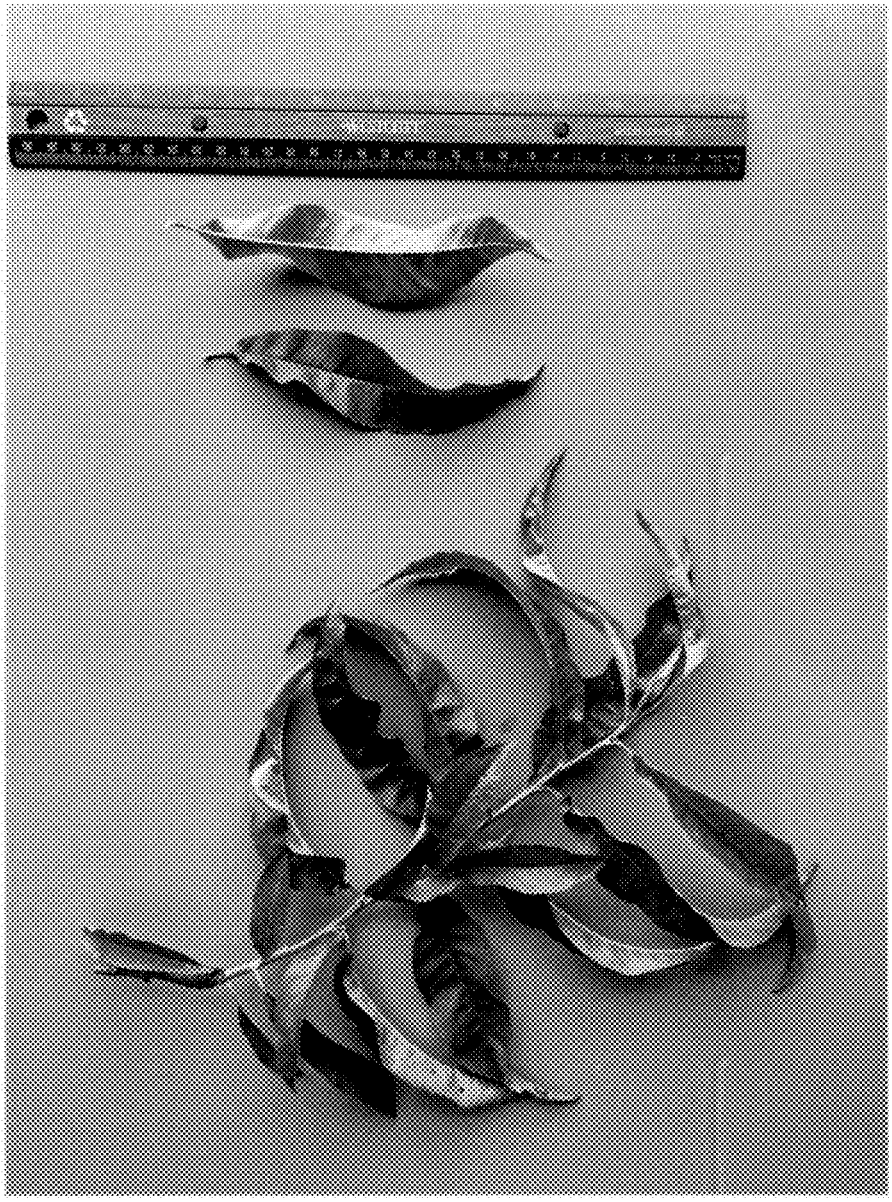
Figure 2:
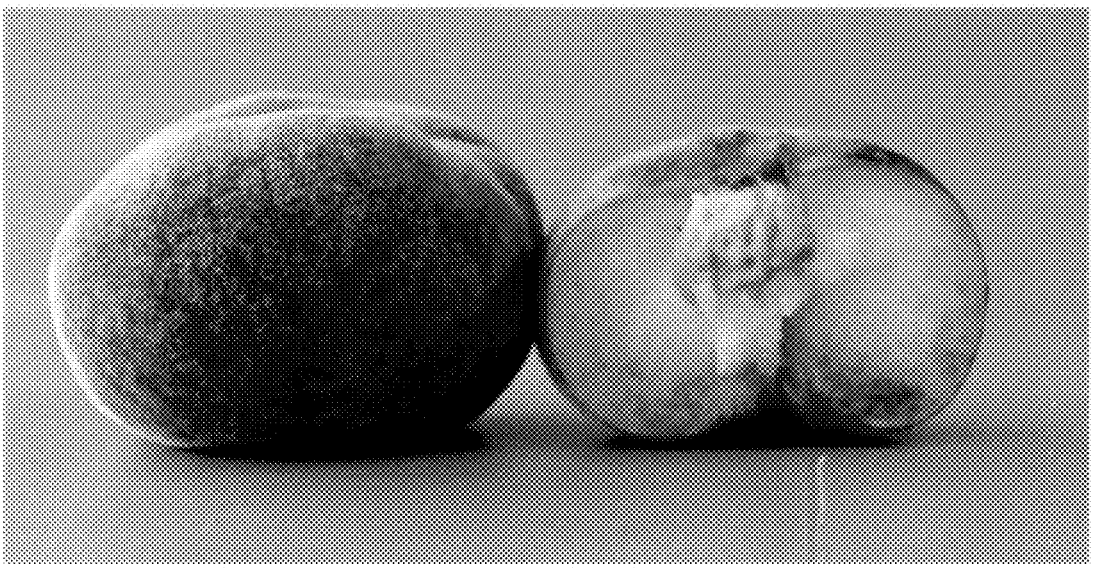
Figure 3:
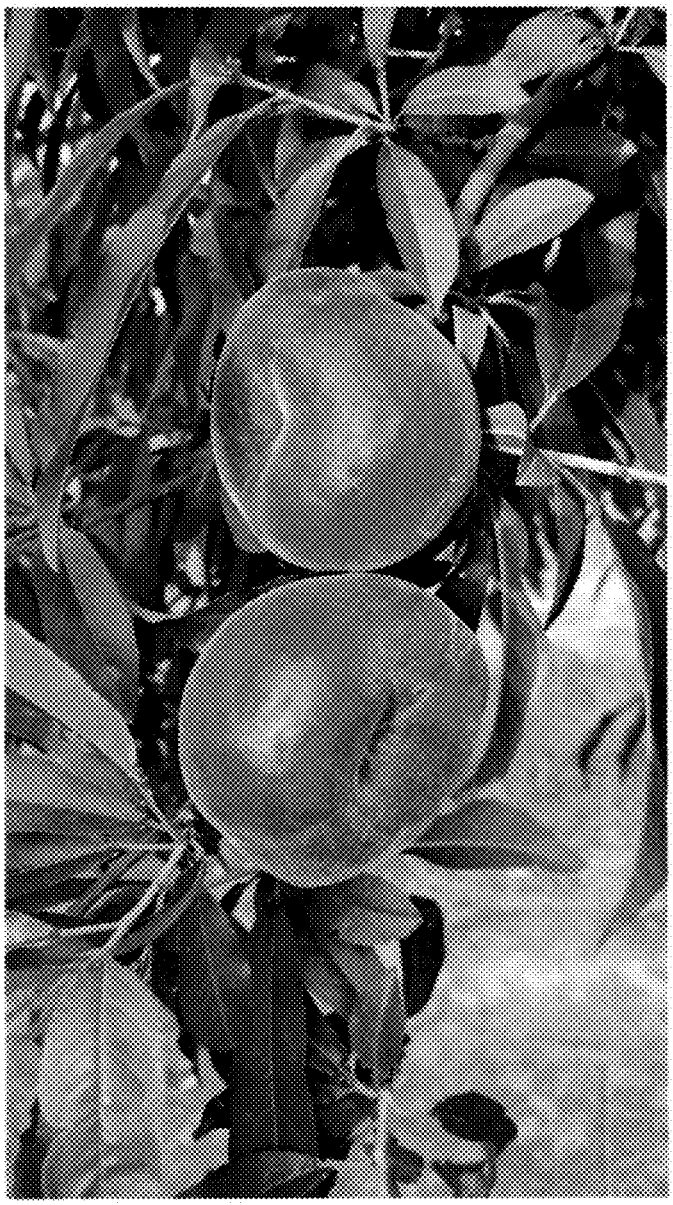
FIG. 3 is a color photograph showing the fruit on a 4-year old 'Flat Delight Three' tree grown in Fairfield, Texas, picture taken Apr. 25, 2017.
Figure 4:
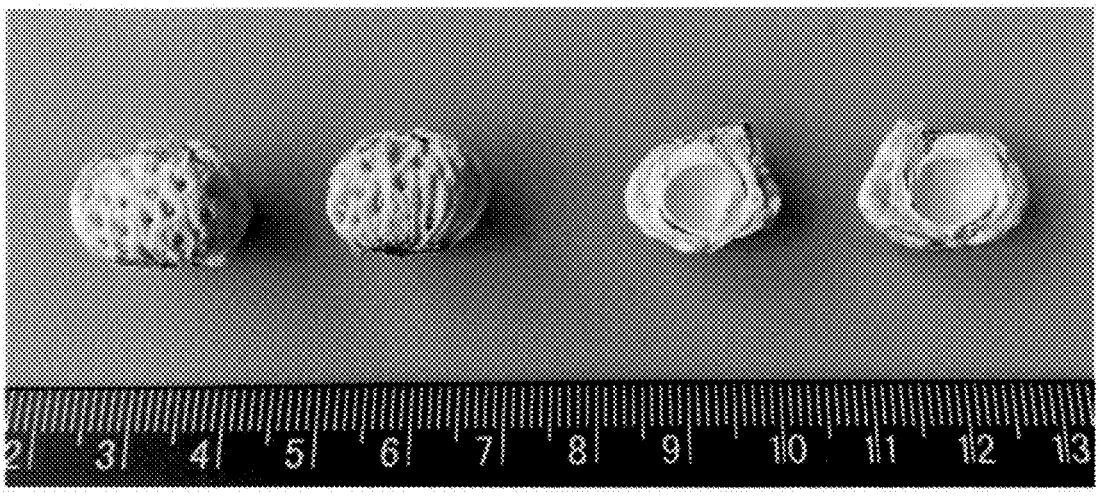
FIG. 4 is a color photograph showing the pits (endocarp) of 'Flat Delight Three' harvested May 3, 2023 in orchard in Fairfield TX. The scale of the ruler is in centimeters.

Referring more specifically to the pomological details of this new and distinct variety of peach tree, the following has been observed under the ecological conditions prevailing at the experimental orchards in the medium chill zone of Texas (Fairfield and College Station). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

- *Size*.—Generally average to above average as compared to other common peach cultivars ripening in the early season of maturity.
- *Height*.—7 to 8 feet (2.1 to 2.4 m) at the end of the 2020 growing season.
- *Width*.—5 feet width (1.5 m) at the end of the 2020 growing season.
- *Density*.—Medium to high.
- *Productivity*.—Produces annually in the medium chill zone of Texas without alternate bearing if temperatures of 28° F. or lower are not experienced during bloom. Trees are self-fertile and must be fruit thinned to avoid limb breakage and obtain optimal fruit size. Trees often set several times the number of fruit needed for a full crop load.
- *Shape*.—The 'Flat Delight Three' peach has been trained in open center configuration. It generally exhibits a spreading and basitonic tropism when compared to average commercial varieties of peach.
- *Current season growth*.—The current season growth for the new variety was approximately 2 to 4 feet (0.6 to 1.2 m). Medium high to high vigor as compared to other commercial cultivars grown in the medium chill zone.
- *Regularity of bearing*.—Regular when not confronted with temperatures below 28° F. in the medium chill zone of Texas.

Trunk:

- *Size*.—Approximately 1.5 to 2 inches (3.8 to 5 cm) in diameter and 5 to 6 inches (12.7 to 15.24 cm) in circumference when measured at a distance of approximately 12 inches (30.5 cm) above the soil level, at the end of the 2020 growing season on a eight-year old tree.
- *Bark texture*.—Considered moderately rough with numerous folds of papery scarf-like skin being present.
- *Bark coloration*.—Variable, colors present are 166A, 176A and 177A of the Greyed-Orange Group, 178A of the Greyed-Red Group, 183A and 183B of the Greyed-Purple Group, N187D of the Greyed-Purple Group, 200A and 200B of the Brown Group and 202D of the Black Group.

Branches:

- *Size*.—Considered medium for the variety.
- *Thickness*.—Average (about 1.8 to 1.9 cm in diameter as measured 10 cm from the trunk on a five-year old tree) as compared to other varieties. Surface Texture — Average and appearing furrowed on wood that is several years old.
- *Lenticels*.—Numerous raised, oval lenticels present. The lenticels range in size from approximately 3 to 6 mm in width and were approximately 1 to 2 mm in height.
- *Current season shoots*.—Surface texture — Substantially glabrous. Internode Length — Approximately 1.3 to 2.2 cm as measured in the middle of a current season stem.
- *Color of mature branches*.—The predominant colors are 165A, 166A, 174A, 175A, 176A, 177A of the Greyed-Orange Group, 178A and 178B of the Greyed-Red Group and 200B of the Brown Group.
- *Current season shoots*.—Color — Light green (144B, 146C, and 146D of Yellow-Green Group) with some reddish-brown coloration appearing on exposed surface of the shoots (166A of the Greyed-Orange Group, 178A of the Greyed-Red Group, 183A, 183B, 187A, and 187B of the Greyed-Purple Group).

Leaves:

- *Size*.—Considered small to medium for the species. Leaf measurements have been taken from vigorous upright current season growth approximately at mid-shoot.
- *Leaf length*.—Approximately 14 to 15 cm.
- *Leaf width*.—Approximately 3.0 to 3.4 cm.
- *Leaf thickness*.—Less than 1 mm.
- *Leaf form*.—Lanceolate.

*Leaf tip form*.—Acuminate.

*Leaf upper surface color*.—Green, 137B and 137C of the Green Group.

*Leaf lower surface color*.—Green varying among 137C and 138B of the Green Group and 146A and 146B of the Yellow-Green Group. Leaf Mid-Vein Color — Light yellow green, 145C and 150D of the Yellow-Green Group.

*Leaf margins*.—

*Form*.—Considered crenate.

*Uniformity*.—Considered generally uniform.

*Leaf petioles*.—

*Size*.—Considered short to medium.

*Length*.—Approximately 8 to 10 mm.

*Thickness*.—Approximately 1 mm.

*Color*.—Pale green 144D, N144A, N144D, and 145D of the Yellow-Green Group.

Leaf glands.—

*Size*.—Approximately 1 mm in height and less than 1 mm in width.

*Number*.—Generally 2-4 per leaf.

*Type*.—Reniform.

*Color*.—Greenish brown 165A, 165B, 166A, 166B, and 166C of the Greyed-Orange Group and 199A, N1990, and N199D of the Grey-Brown Group.

*Leaf stipules*.—

*Size*.—Small to medium for the variety.

*Length*.—Approximately 10 to 11 mm.

*Form*.—Lanceolate.

*Color*.—Light-medium green (144B, 144C, N144D, 145A, 145B, 146C, and 146D of the Yellow-Green Group) with light maroon tips (181B and 182A of the Greyed-Red Group and 183D, 184C, 184D, 185C, and 186A of the Greyed-Purple Group) when young. The stipules are early deciduous.

*Ratio of wood (leaf) buds to flowering buds*.—Generally 2 flower buds per vegetative bud.

Flowers:

*Floral buds*.—

*General*.—The floral buds are conic in form, and slightly appressed relative to the bearing shoot.

*Color*.—The bud scales are medium brown, (approximately 165A and 166A of the Greyed-Brown Group and N199B and N199C of the Grey-Brown Group). The buds are considered hardy under typical climatic conditions of the medium chill zone of Texas.

*Length*.—Approximately 1 to 3 mm in late summer.

*Blooming type*.—Considered early in relation to other peach cultivars commonly growing in the medium chill zone of Texas. Date of full bloom was between February 6$^{th}$ and February 27$^{th}$ (mean February 18$^{th}$) during the period between 2014 and 2020.

*Flower type*.—Showy.

*Flower size*.—Flower diameter at full bloom is approximately 37 to 40 mm.

*Bloom quantity*.—Considered abundant.

*Flower bud frequency*.—Normally 1 to 2 per node.

*Petal size*.—

*General*.—Considered large for the species.

*Width*.—Approximately 15 to 16 mm.

*Length*.—Approximately 20 to 21 mm.

*Petal form*.—Broadly ovate.

*Petal count*.—Nearly always 5.

*Petal color*.—Medium pink when young (62C, 62D, 65B, 65C, 65D, 69A, 69B, and 73D of the Red-Purple Group), becoming darker near the petal claw.

*Petal claw*.—

*Form*.—The claw is considered truncate in shape and has a medium size when compared to other varieties.

*Length*.—Approximately 1 to 2 mm.

*Width*.—Approximately 1 mm.

*Petal margins*.—Generally considered variable, from nearly smooth to slightly undulate.

*Petal apex*.—Generally — The petal apices appear slightly rounded.

*Flower pedicel*.—

*Length*.—Considered short, and having an average length of 2 to 3 mm.

*Thickness*.—Considered average, approximately 1 mm.

*Color*.—A light green (N144D, 145A, and 145B of the Yellow-Green Group).

*Floral nectaries*.—

*Color*.—Light to medium orange (13B, 13C, 14A, 14B, and 14C of the Yellow Group and 15A, 15B, and 15C of the Yellow-Orange Group).

*Nectar cup*.—

*Surface texture*.—Generally glabrous.

*Color*.—Maroon with green (approximately 58A, 59B, 59C, 60A, and 60B of the Red-Purple Group and 144B, 144C, 144D, N144D, 145A, and 145B of the Yellow-Green Group).

Sepals.—

*Surface texture*.—The surface has a short, fine, wooly and a gray-colored texture.

*Size*.—Average, and ovate in form.

*Color*.—Maroon and green with white texture (approximately 58A, 59B, 59C, 60A, and 60B of the Red-Purple Group; 144B, 144C, 144D, N144D, 145A, and 145B of the Yellow-Green Group and 155A, 155B, 155C, and 155D of the White Group).

*Anthers*.—

*General*.—Average in size for the species.

*Color*.—Medium to dark orange (approximately N25B, N25C, 28A, and 28B of the Orange Group and 30B, 30C, 30D, and N30D of the Orange-Red Group).

*Pollen production*.—Pollen is abundant and a medium yellow color (approximately 5A, 5B, 5C, 6A, 6B, 6C, 9A, 9B, and 9C of the Yellow Group and 14B, 15A, 15B, and 15C of the Yellow-Orange Group).

*Filaments*.—

*Size*.—Variable in length, approximately 9 to 16 mm, with the filaments slightly longer than the pistil height.

*Color*.—White (approximately 155A, 155B, 155C, and 155D of the White Group) and darkening with advanced maturity.

*Pistil*.—

*General*.—Shorter than average, about same or slightly shorter than anther height.

*Length*.—Approximately 12 to 14 mm, including the ovary.

*Color*.—Considered a light yellow-green when young (approximately 1A, 1B, 1C, and 1D of the Green-Yellow Group and 154C and 154D of the Yellow-Green Group), and becoming slightly darker with advancing senescence.

*Surface texture.*—The variety has a long, silver white pubescent pistil (approximately 155A, 155B, 155C, and 155D of the White Group).

Fruit:

*Maturity when described.*—The present variety of fruit is described, as it would be found in its firm ripe condition at full commercial maturity. Under the ecological conditions prevailing in the medium chill zone of Texas it would be ripe in early May. The average ripe date at College Station is May 7$^{th}$.

*Size.*—General — Medium to medium large for the season and considered uniform.

*Average cheek diameter.*—Approximately 55 to 60 mm.

*Average suture diameter.*—Approximately 56 to 61 mm.

*Average axial diameter.*—Approximately 30 to 34 mm.

*Fruit form.*—Generally considered flat with unequal halves. Occasionally the fruit exhibits less symmetry when comparing the suture height with the line opposite the suture. The fruit is generally uniform in symmetry when viewed from the apical aspect.

*Fruit suture.*—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm.

*Color.*—Dark maroon, 46A and 53A of the Red Group, 59A, 59B, and 60A of the Red-Purple Group and 183A, 183B, 184A, 185A, N186C, 187A, and 187B of the Greyed-Purple Group.

*Ventral surface.*—Form — Considered uniform.

*Stem cavity.*—

*Size.*—Considered moderately shallow for the species.

*Width.*—Approximately 16 to 21 mm.

*Length.*—Approximately 23 to 32 mm.

*Depth.*—Approximately 4 to 5 mm.

*Fruit base.*—Flat.

*Fruit apex.*—Flat.

*Fruit stem.*—

*Length.*—7 to 8 mm.

*Thickness.*—Approximately 3 mm.

*Color.*—Varies from medium to dark brown with green, 144A, 144B, 146C, 146D, and 147C of the Yellow-Green Group to 165A, 165B, 166A, and 166B of the Greyed-Orange Group.

*Fruit skin.*—Generally considered medium or average in thickness.

*Surface texture.*—Light, short pubescence.

*Skin acidity.*—Considered neutral.

*Tenacious to flesh.*—Yes at commercial maturity.

*Tendency to crack.*—Not observed.

*Skin color.*—Generally — Variable, with approximately 50-80% of the fruit surface covered with a dark pink to dark maroon blush.

*Blush color.*—Dark pink to dark maroon, 53A and 53B of the Red Group, 59A, 59B, 59C, 60A, 60B, and 60C of the Red-Purple Group and N77A and N79A of the Purple Group.

*Skin ground color.*—Light yellow, 1C and 1D of the Green-Yellow Group and 2C, 2D, 3C, 3D, 4C, 4D, 5D, 6D, 8C, 8D, and 9D of the Yellow Group.

*Flesh color.*—White with a medium pink, 51A of the Red Group, 63A, 63B, and 67A of the Red-Purple Group and 155A, 155B, 155C, and 155D of the White Group.

*Flesh fibers.*—Present, numerous and lightly colored. These fibers are present throughout the flesh.

*Stone cavity color.*—White, 155A, 155B, 155C, and 155D of the White Group.

*Flesh texture.*—Generally, the flesh is considered firm and fine at commercial maturity.

*Ripening.*—Generally the fruit of the present variety ripens evenly.

*Flavor.*—Subacid sweet flavor.

*Aroma.*—Pleasant and reasonably abundant.

*Eating.*—Generally considered very good, particularly for an early ripening variety.

Stone:

*Attachment.*—Clingstone at commercial maturity.

*Stone size.*—Generally considered medium to medium-large relative to the ratio of stone to fruit size.

*Length.*—Approximately 12 to 13 mm.

*Width.*—Approximately 15 to 17 mm.

*Thickness.*—Approximately 17 mm.

*Fibers.*—Generally a few medium length fibers are attached along the entire surface of the stone.

*Stone form.*—Flat.

*Stone base.*—The stone base is very wide.

*Apex shape.*—Very wide.

*Stone shape.*—Considered flat.

*Stone surface.*—

*Surface texture.*—Single Pits.

*Ridges.*—Numerous fine ridges are present basally and converge towards the base of the stone.

*Ventral edge.*—None.

*Dorsal edge.*—Shape — Grooved and having moderately rough edges.

*Stone color.*—The color of the dry stone is tan, 158A of the Yellow-White Group, 159A of the Orange-White Group and 164D and 165D of the Greyed-Orange Group. The color of the inside surface of the endocarp is primarily light tan, 158B, 158C, and 158D of the Yellow-White Group, 159D of the Orange-White Group and 164D of the Greyed-Orange Group.

*Tendency to split.*—Splitting is relatively uncommon.

*Kernel.*—The kernel fills the endocarp at harvest and measures approximately 3-4 mm in thickness, 5-7 mm in width and 6-8 mm in length. The colors of the fresh kernels are variable from ivory to medium brown, 155B and 155D of the White Group, 161A and 161B of the Greyed-Yellow Group and 164A, 164B, 164C, 165B, and 165C of the Greyed-Orange Group. When dried the shriveled kernels measure approximately 2-3 mm in thickness, 4-5 mm in width and 5-6 mm in length. The colors of the shriveled kernels are light to medium brown, 163A, 164A, 164B, 165B, 165C, and N167A of the Greyed-Orange Group.

*Use.*—The subject variety, 'Flat Delight Three', is considered to be a peach tree of early-season maturity, which produces subacid, white-fleshed flat peach fruit which are very firm, with the skin covered with a dark pink to dark maroon blush over 50-80% of its surface, and which are useful for both local and long distance shipping.

*Keeping quality*.—Good to very good. Retains firmness and flavor after 14 days of refrigeration at 3-5° C.

*Resistance to insects and disease*.—No atypical resistances/susceptibilities have been noted under normal cultural practices to date.

*Shipping quality*.—Average. Degree of firmness at harvest and firmness retained in refrigeration for approximately 14 days at 3-5° C. with no internal breakdown of flesh or appreciable loss of eating quality indicates fruit should be acceptable for shipping.

Although the new variety of peach tree possesses the described characteristics when grown under the ecological conditions prevailing in the medium chill zone of Texas in College Station and Fairfield, it will be understood that variations of the usual magnitude and characteristics incident to the changes in growing conditions, fertilization, pruning, and pest control are to be expected.

The invention claimed is:

1. A new and distinct *Prunus persica* tree named 'Flat Delight Three' as illustrated and described herein.

* * * * *